United States Patent
Oestdal et al.

(10) Patent No.: US 11,834,484 B2
(45) Date of Patent: Dec. 5, 2023

(54) BAKERS'S YEAST EXPRESSING ANTI-STALING/FRESHNESS AMYLASES

(71) Applicant: Novozymes A/S, Bagsvaerd (DK)

(72) Inventors: Henrik Oestdal, Virum (DK); Monica Tassone, West Sacramento, CA (US); Michael Glenn Catlett, West Sacramento, CA (US); David Hogsett, Auburn, CA (US); Michael Nielsen, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 518 days.

(21) Appl. No.: 16/640,792

(22) PCT Filed: Aug. 28, 2018

(86) PCT No.: PCT/EP2018/073091
§ 371 (c)(1),
(2) Date: Feb. 21, 2020

(87) PCT Pub. No.: WO2019/042971
PCT Pub. Date: Mar. 7, 2019

(65) Prior Publication Data
US 2021/0155943 A1  May 27, 2021

Related U.S. Application Data

(60) Provisional application No. 62/551,318, filed on Aug. 29, 2017.

(51) Int. Cl.
| | | |
|---|---|---|
| *C07K 14/54* | (2006.01) | |
| *A21D 8/04* | (2006.01) | |
| *A61K 38/20* | (2006.01) | |
| *A61P 37/04* | (2006.01) | |
| *C07K 14/715* | (2006.01) | |
| *C12N 15/81* | (2006.01) | |
| *A61K 38/00* | (2006.01) | |

(52) U.S. Cl.
CPC .......... *C07K 14/5443* (2013.01); *A21D 8/047* (2013.01); *A61K 38/2086* (2013.01); *A61P 37/04* (2018.01); *C07K 14/54* (2013.01); *C07K 14/5418* (2013.01); *C07K 14/7155* (2013.01); *C12N 15/81* (2013.01); *A61K 38/00* (2013.01); *C07K 2319/00* (2013.01); *C07K 2319/02* (2013.01); *C07K 2319/30* (2013.01); *C12Y 302/01002* (2013.01); *C12Y 302/01033* (2013.01)

(58) Field of Classification Search
None
See application file for complete search history.

(56) References Cited

U.S. PATENT DOCUMENTS

| | | | |
|---|---|---|---|
| 6,667,065 B1 | 12/2003 | Kragh et al. | |
| 7,166,453 B2 * | 1/2007 | Kragh | A23K 20/189 536/23.74 |
| 8,895,088 B2 * | 11/2014 | Matsunaga | C12Y 302/01002 426/531 |
| 2005/0136524 A1 | 6/2005 | Kragh | |
| 2009/0203108 A1 | 8/2009 | Cherry et al. | |
| 2012/0121760 A1 | 5/2012 | Matsunaga et al. | |
| 2012/0301927 A1 | 11/2012 | Duan et al. | |
| 2015/0373999 A1 | 12/2015 | Van Benschop | |

FOREIGN PATENT DOCUMENTS

| | | |
|---|---|---|
| CN | 102277308 A | 12/2011 |
| CN | 102388133 A | 3/2012 |
| CN | 102595910 A | 7/2012 |
| CN | 107201373 A | 9/2017 |
| EP | 0120693 A1 | 10/1984 |
| EP | 0289138 A2 | 11/1988 |
| EP | 2295563 A1 | 3/2011 |
| NO | 2000/29591 A1 | 5/2000 |
| WO | 1999/43794 A1 | 9/1999 |
| WO | 2001/16349 A1 | 3/2001 |
| WO | 2012/010592 A1 | 1/2012 |
| WO | 2018/167669 A1 | 9/2018 |

OTHER PUBLICATIONS

Nieto et al. (Stable High-Copy-Number Integration of *Aspergillus oryzae* r-AMYLASE cDNA in an Industrial Baker's Yeast Strain, Biotechnol. Prog. 1999, 15, 459-466).*
Gandhi et al, 2015, Biomed research international 2015, pp. 1-9.
Goesaert et al, 2009, J Cereal Sci, vol. 50, No. 3, pp. 345-352.
Nieto et al, 1999, Biotechnol Progr, vol. 15, pp. 459-466.
Park et al, 2018, Food sci biotechnol, vol. 27, No. 2, pp. 299-312.
Randez-Gil et al, 1995, J Cereal Sci, vol. 21, pp. 185-193.
Roberto et al, 1988, Biochem Biophys Res Com, vol. 152, No. 1, pp. 76-82.
Shim et al, 2007, J Agric Food Chem, vol. 55, pp. 4735-4740.
Jeda et al, 2000, J Biosci Bioeng, vol. 90, No. 2, pp. 125-136.
Wang et al, 2010, J Microbiol Biotechnol, vol. 20, No. 11, pp. 1539-1545.

* cited by examiner

*Primary Examiner* — Suzanne M Noakes
*Assistant Examiner* — Jae W Lee
(74) *Attorney, Agent, or Firm* — Yoshimi Barron

(57) ABSTRACT

A recombinant yeast cell comprising a heterologous polynucleotide encoding an anti-staling/freshness amylase; in particular an anti-staling/freshness amylase selected from the group consisting of a maltogenic amylase (EC 3.2.1.133), a beta-amylase (EC 3.2.1.2), and a glucan 1,4-alpha-maltotetrahydrolase (EC 3.2.1.60).

9 Claims, No Drawings
Specification includes a Sequence Listing.

SEQUENCE LISTING

```
<160> NUMBER OF SEQ ID NOS: 8

<210> SEQ ID NO 1
<211> LENGTH: 705
<212> TYPE: PRT
<213> ORGANISM: Bacillus stearothermophilus

<400> SEQUENCE: 1

Met Arg Phe Pro Ser Ile Phe Thr Thr Val Leu Phe Ala Ala Ser Ser
1               5                   10                  15

Ala Leu Ala Ser Ser Ser Ala Ser Val Lys Gly Asp Val Ile Tyr Gln
                20                  25                  30

Ile Ile Ile Asp Arg Phe Tyr Asp Gly Asp Thr Thr Asn Asn Asn Pro
            35                  40                  45

Ala Lys Ser Tyr Gly Leu Tyr Asp Pro Thr Lys Ser Lys Trp Lys Met
        50                  55                  60

Tyr Trp Gly Gly Asp Leu Glu Gly Val Arg Gln Lys Leu Pro Tyr Leu
65                  70                  75                  80

Lys Gln Leu Gly Val Thr Thr Ile Trp Leu Ser Pro Val Leu Asp Asn
                85                  90                  95

Leu Asp Thr Leu Ala Gly Thr Asp Asn Thr Gly Tyr His Gly Tyr Trp
            100                 105                 110

Thr Arg Asp Phe Lys Gln Ile Glu Glu His Phe Gly Asn Trp Thr Thr
        115                 120                 125

Phe Asp Thr Leu Val Asn Asp Ala His Gln Asn Gly Ile Lys Val Ile
    130                 135                 140

Val Asp Phe Val Pro Asn His Ser Thr Pro Phe Lys Ala Asn Asp Ser
145                 150                 155                 160

Thr Phe Ala Glu Gly Gly Ala Leu Tyr Asn Asn Gly Thr Tyr Met Gly
                165                 170                 175
```

```
Asn Tyr Phe Asp Asp Ala Thr Lys Gly Tyr Phe His His Asn Gly Asp
            180                 185                 190
Ile Ser Asn Trp Asp Asp Arg Tyr Glu Ala Gln Trp Lys Asn Phe Thr
        195                 200                 205
Asp Pro Ala Gly Phe Ser Leu Ala Asp Leu Ser Gln Glu Asn Gly Thr
210                 215                 220
Ile Ala Gln Tyr Leu Thr Asp Ala Ala Val Gln Leu Ala His Gly
225                 230                 235                 240
Ala Asp Gly Leu Arg Ile Asp Ala Val Lys His Phe Asn Ser Gly Phe
                245                 250                 255
Ser Lys Ser Leu Ala Asp Lys Leu Tyr Gln Lys Lys Asp Ile Phe Leu
            260                 265                 270
Val Gly Glu Trp Tyr Gly Asp Asp Pro Gly Thr Ala Asn His Leu Glu
        275                 280                 285
Lys Val Arg Tyr Ala Asn Asn Ser Gly Val Asn Val Leu Asp Phe Asp
        290                 295                 300
Leu Asn Thr Val Ile Arg Asn Val Phe Gly Thr Phe Thr Gln Thr Met
305                 310                 315                 320
Tyr Asp Leu Asn Asn Met Val Asn Gln Thr Gly Asn Glu Tyr Lys Tyr
                325                 330                 335
Lys Glu Asn Leu Ile Thr Phe Ile Asp Asn His Asp Met Ser Arg Phe
            340                 345                 350
Leu Ser Val Asn Ser Asn Lys Ala Asn Leu His Gln Ala Leu Ala Phe
        355                 360                 365
Ile Leu Thr Ser Arg Gly Thr Pro Ser Ile Tyr Tyr Gly Thr Glu Gln
        370                 375                 380
Tyr Met Ala Gly Gly Asn Asp Pro Tyr Asn Arg Gly Met Met Pro Ala
385                 390                 395                 400
Phe Asp Thr Thr Thr Thr Ala Phe Lys Glu Val Ser Thr Leu Ala Gly
                405                 410                 415
Leu Arg Arg Asn Asn Ala Ala Ile Gln Tyr Gly Thr Thr Thr Gln Arg
            420                 425                 430
Trp Ile Asn Asn Asp Val Tyr Ile Tyr Glu Arg Lys Phe Phe Asn Asp
        435                 440                 445
Val Val Leu Val Ala Ile Asn Arg Asn Thr Gln Ser Ser Tyr Ser Ile
450                 455                 460
Ser Gly Leu Gln Thr Ala Leu Pro Asn Gly Ser Tyr Ala Asp Tyr Leu
465                 470                 475                 480
Ser Gly Leu Leu Gly Gly Asn Gly Ile Ser Val Ser Asn Gly Ser Val
                485                 490                 495
Ala Ser Phe Thr Leu Ala Pro Gly Ala Val Ser Val Trp Gln Tyr Ser
            500                 505                 510
Thr Ser Ala Ser Ala Pro Gln Ile Gly Ser Val Ala Pro Asn Met Gly
        515                 520                 525
Ile Pro Gly Asn Val Val Thr Ile Asp Gly Lys Gly Phe Gly Thr Thr
        530                 535                 540
Gln Gly Thr Val Thr Phe Gly Gly Val Thr Ala Thr Val Lys Ser Trp
545                 550                 555                 560
Thr Ser Asn Arg Ile Glu Val Tyr Val Pro Asn Met Ala Ala Gly Leu
                565                 570                 575
Thr Asp Val Lys Val Thr Ala Gly Gly Val Ser Ser Asn Leu Tyr Ser
            580                 585                 590
```

Tyr Asn Ile Leu Ser Gly Thr Gln Thr Ser Val Val Phe Thr Val Lys
            595                 600                 605

Ser Ala Pro Pro Thr Asn Leu Gly Asp Lys Ile Tyr Leu Thr Gly Asn
610                 615                 620

Ile Pro Glu Leu Gly Asn Trp Ser Thr Asp Thr Ser Gly Ala Val Asn
625                 630                 635                 640

Asn Ala Gln Gly Pro Leu Leu Ala Pro Asn Tyr Pro Asp Trp Phe Tyr
            645                 650                 655

Val Phe Ser Val Pro Ala Gly Lys Thr Ile Gln Phe Lys Phe Ile
            660                 665                 670

Lys Arg Ala Asp Gly Thr Ile Gln Trp Glu Asn Gly Ser Asn His Val
            675                 680                 685

Ala Thr Thr Pro Thr Gly Ala Thr Gly Asn Ile Thr Val Thr Trp Gln
690                 695                 700

Asn
705

<210> SEQ ID NO 2
<211> LENGTH: 705
<212> TYPE: PRT
<213> ORGANISM: Artificial sequence
<220> FEATURE:
<223> OTHER INFORMATION: Synthetic construct

<400> SEQUENCE: 2

Met Arg Phe Pro Ser Ile Phe Thr Thr Val Leu Phe Ala Ala Ser Ser
1               5                   10                  15

Ala Leu Ala Ser Ser Ala Ser Val Lys Gly Asp Val Ile Tyr Gln
            20                  25                  30

Ile Ile Ile Asp Arg Phe Tyr Asp Gly Asp Thr Thr Asn Asn Asn Pro
            35                  40                  45

Ala Lys Ser Tyr Gly Leu Tyr Asp Pro Thr Lys Ser Lys Trp Lys Met
50                  55                  60

Tyr Trp Gly Gly Asp Leu Glu Gly Val Arg Gln Lys Leu Pro Tyr Leu
65                  70                  75                  80

Lys Gln Leu Gly Val Thr Thr Ile Trp Leu Ser Pro Val Leu Asp Asn
            85                  90                  95

Leu Asp Thr Leu Ala Gly Thr Asp Asn Thr Gly Tyr His Gly Tyr Trp
            100                 105                 110

Thr Arg Asp Phe Lys Gln Ile Glu Glu His Phe Gly Asn Trp Thr Thr
            115                 120                 125

Phe Asp Thr Leu Val Asn Asp Ala His Gln Asn Gly Ile Lys Val Ile
130                 135                 140

Val Asp Phe Val Pro Asn His Ser Thr Pro Phe Lys Ala Asn Asp Ser
145                 150                 155                 160

Thr Phe Ala Glu Gly Gly Ala Leu Tyr Asn Asn Gly Thr Tyr Met Gly
            165                 170                 175

Asn Tyr Phe Asp Asp Ala Thr Lys Gly Tyr Phe His His Asn Gly Asp
            180                 185                 190

Ile Ser Asn Trp Asp Asp Arg Tyr Glu Ala Gln Trp Lys Asn Leu Thr
            195                 200                 205

Asp Pro Ala Gly Phe Ser Leu Ala Asp Leu Ser Gln Glu Asn Gly Thr
210                 215                 220

Ile Ala Gln Tyr Leu Thr Asp Ala Ala Val Gln Leu Val Ala His Gly
225                 230                 235                 240

-continued

Ala Asp Gly Leu Arg Ile Asp Ala Val Lys His Phe Asn Ser Gly Phe
            245                 250                 255

Ser Lys Ser Leu Ala Asp Lys Leu Tyr Gln Lys Lys Asp Ile Phe Leu
        260                 265                 270

Val Gly Glu Trp Tyr Gly Asp Gly Pro Gly Thr Ala Asn His Leu Glu
    275                 280                 285

Lys Val Arg Tyr Ala Asn Asn Ser Gly Val Asn Val Leu Asp Phe Asp
290                 295                 300

Leu Asn Pro Val Ile Arg Asn Val Phe Gly Thr Phe Thr Gln Thr Met
305                 310                 315                 320

Tyr Asp Leu Asn Asn Met Val Asn Gln Thr Gly Asn Glu Tyr Lys Tyr
                325                 330                 335

Lys Glu Asn Leu Ile Thr Phe Ile Asp Asn His Asp Met Ser Arg Phe
            340                 345                 350

Leu Ser Val Asn Ser Asn Lys Ala Asn Leu His Gln Ala Leu Ala Phe
        355                 360                 365

Ile Leu Thr Ser Arg Gly Thr Pro Ser Ile Tyr Tyr Gly Thr Glu Gln
    370                 375                 380

Tyr Met Ala Gly Gly Asn Asp Pro Tyr Asn Arg Gly Met Met Pro Ala
385                 390                 395                 400

Phe Asp Thr Thr Thr Thr Ala Phe Lys Glu Val Ser Thr Leu Ala Gly
                405                 410                 415

Leu Arg Arg Asn Asn Ala Ala Ile Gln Tyr Gly Thr Thr Thr Gln Arg
            420                 425                 430

Trp Ile Asn Asn Asp Val Tyr Ile Tyr Glu Arg Lys Phe Phe Asn Asp
        435                 440                 445

Val Val Leu Val Ala Ile Asn Arg Asn Thr Gln Ser Ser Tyr Ser Ile
    450                 455                 460

Ser Gly Leu Gln Thr Ala Leu Pro Asn Gly Ser Tyr Ala Asp Tyr Leu
465                 470                 475                 480

Ser Gly Leu Leu Gly Gly Asn Gly Ile Ser Val Ser Asn Gly Ser Val
                485                 490                 495

Ala Ser Phe Thr Leu Ala Pro Gly Ala Val Ser Val Trp Gln Tyr Ser
            500                 505                 510

Thr Ser Ala Ser Ala Pro Gln Ile Gly Ser Val Ala Pro Asn Met Gly
        515                 520                 525

Ile Pro Gly Asn Val Val Thr Ile Asp Gly Lys Gly Phe Gly Thr Thr
    530                 535                 540

Gln Gly Thr Val Thr Phe Gly Gly Val Thr Ala Thr Val Lys Ser Trp
545                 550                 555                 560

Thr Ser Asn Arg Ile Glu Val Tyr Val Pro Asn Met Ala Ala Gly Leu
                565                 570                 575

Thr Asp Val Lys Val Thr Ala Gly Gly Val Ser Ser Asn Leu Tyr Ser
            580                 585                 590

Tyr Asn Ile Leu Ser Gly Thr Gln Thr Ser Val Val Phe Thr Val Lys
        595                 600                 605

Ser Ala Pro Pro Thr Asn Leu Gly Asp Lys Ile Tyr Leu Thr Gly Asn
    610                 615                 620

Ile Pro Glu Leu Gly Asn Trp Ser Thr Asp Thr Ser Gly Ala Val Asn
625                 630                 635                 640

Asn Ala Gln Gly Pro Leu Leu Ala Pro Asn Tyr Pro Asp Trp Phe Tyr
                645                 650                 655

Val Phe Ser Val Pro Ala Gly Lys Thr Ile Gln Phe Lys Phe Phe Ile

-continued

```
              660                 665                 670
Lys Arg Ala Asp Gly Thr Ile Gln Trp Glu Asn Gly Ser Asn His Val
            675                 680                 685
Ala Thr Thr Pro Thr Gly Ala Thr Gly Asn Ile Thr Val Thr Trp Gln
            690                 695                 700
Asn
705

<210> SEQ ID NO 3
<211> LENGTH: 705
<212> TYPE: PRT
<213> ORGANISM: Artificial sequence
<220> FEATURE:
<223> OTHER INFORMATION: Synthetic construct

<400> SEQUENCE: 3

Met Arg Phe Pro Ser Ile Phe Thr Thr Val Leu Phe Ala Ala Ser Ser
1               5                   10                  15
Ala Leu Ala Ser Ser Ala Ser Val Lys Gly Asp Val Ile Tyr Gln
            20                  25                  30
Ile Ile Ile Asp Arg Phe Tyr Asp Gly Asp Thr Thr Asn Asn Asn Pro
        35                  40                  45
Ala Lys Ser Tyr Gly Leu Tyr Asp Pro Thr Lys Ser Lys Trp Lys Met
    50                  55                  60
Tyr Trp Gly Gly Asp Leu Glu Gly Val Arg Gln Lys Leu Pro Tyr Leu
65                  70                  75                  80
Lys Gln Leu Gly Val Thr Thr Ile Trp Leu Ser Pro Val Leu Asp Asn
                85                  90                  95
Leu Asp Thr Leu Ala Gly Thr Asp Asn Thr Gly Tyr His Gly Tyr Trp
            100                 105                 110
Thr Arg Asp Phe Lys Gln Ile Glu Glu His Phe Gly Asn Trp Thr Thr
        115                 120                 125
Phe Asp Thr Leu Val Asn Asp Ala His Gln Asn Gly Ile Lys Val Ile
    130                 135                 140
Val Asp Phe Val Pro Asn His Ser Thr Pro Phe Lys Ala Asn Asp Ser
145                 150                 155                 160
Thr Phe Ala Glu Gly Gly Ala Leu Tyr Asn Asn Gly Thr Tyr Met Gly
                165                 170                 175
Asn Tyr Phe Asp Asp Ala Thr Lys Gly Tyr Phe His His Asn Gly Asp
            180                 185                 190
Ile Ser Asn Trp Asp Asp Arg Tyr Glu Ala Gln Trp Lys Asn Phe Thr
        195                 200                 205
Asp Pro Ala Gly Tyr Ser Leu Ala Asp Leu Ser Gln Glu Asn Gly Thr
    210                 215                 220
Ile Ala Gln Tyr Leu Thr Asp Ala Ala Val Gln Leu Val Ala His Gly
225                 230                 235                 240
Ala Asp Gly Leu Arg Ile Asp Ala Val Lys His Phe Asn Ser Gly Phe
                245                 250                 255
Ser Lys Ser Leu Ala Asp Lys Leu Tyr Gln Lys Lys Asp Ile Phe Leu
            260                 265                 270
Val Gly Glu Trp Tyr Gly Asp Gly Pro Gly Thr Ala Asn His Leu Glu
        275                 280                 285
Lys Val Arg Tyr Ala Asn Asn Ser Gly Val Asn Val Leu Asp Phe Asp
    290                 295                 300
Leu Asn Pro Val Ile Arg Asn Val Phe Gly Thr Phe Thr Gln Thr Met
```

```
            305                 310                 315                 320
Tyr Asp Leu Asn Asn Met Val Asn Gln Thr Gly Asn Glu Tyr Lys Tyr
                325                 330                 335
Lys Glu Asn Leu Ile Thr Phe Ile Asp Asn His Asp Met Ser Arg Phe
                340                 345                 350
Leu Ser Val Asn Ser Asn Lys Ala Asn Leu His Gln Ala Leu Ala Phe
                355                 360                 365
Ile Leu Thr Ser Arg Gly Thr Pro Ser Ile Tyr Tyr Gly Thr Glu Gln
            370                 375                 380
Tyr Met Ala Gly Gly Asn Asp Pro Tyr Ser Arg Gly Met Met Pro Ala
385                 390                 395                 400
Phe Asp Thr Thr Thr Ala Phe Lys Glu Val Ser Thr Leu Ala Gly
                405                 410                 415
Leu Arg Arg Asn Asn Ala Ala Ile Gln Tyr Gly Thr Thr Gln Arg
                420                 425                 430
Trp Ile Asn Asn Asp Val Tyr Ile Tyr Glu Arg Lys Phe Phe Asn Asp
                435                 440                 445
Val Val Leu Val Ala Ile Asn Arg Asn Thr Gln Ser Ser Tyr Ser Ile
            450                 455                 460
Ser Gly Leu Gln Thr Ala Leu Pro Asn Gly Ser Tyr Ala Asp Tyr Leu
465                 470                 475                 480
Ser Gly Leu Leu Gly Gly Asn Gly Ile Ser Val Ser Asn Gly Ser Val
                485                 490                 495
Ala Ser Phe Thr Leu Ala Pro Gly Ala Val Ser Val Trp Gln Tyr Ser
                500                 505                 510
Thr Ser Ala Ser Ala Pro Gln Ile Gly Ser Val Ala Pro Asn Met Gly
            515                 520                 525
Ile Pro Gly Asn Val Val Thr Ile Asp Gly Lys Gly Phe Gly Thr Thr
            530                 535                 540
Gln Gly Thr Val Thr Phe Gly Gly Val Thr Ala Thr Val Lys Ser Trp
545                 550                 555                 560
Thr Ser Asn Arg Ile Glu Val Tyr Val Pro Asn Met Ala Ala Gly Leu
                565                 570                 575
Thr Asp Val Lys Val Thr Ala Gly Gly Val Ser Ser Asn Leu Tyr Ser
                580                 585                 590
Tyr Asn Ile Leu Ser Gly Thr Gln Thr Ser Val Phe Thr Val Lys
            595                 600                 605
Ser Ala Pro Pro Thr Asn Leu Gly Asp Lys Ile Tyr Leu Thr Gly Asn
610                 615                 620
Ile Pro Glu Leu Gly Asn Trp Ser Thr Asp Thr Ser Gly Ala Val Asn
625                 630                 635                 640
Asn Ala Gln Gly Pro Leu Leu Ala Pro Asn Tyr Pro Asp Trp Phe Tyr
                645                 650                 655
Val Phe Ser Val Pro Ala Gly Lys Thr Ile Gln Phe Lys Phe Phe Ile
                660                 665                 670
Lys Arg Ala Asp Gly Thr Ile Gln Trp Glu Asn Gly Ser Asn His Val
                675                 680                 685
Ala Thr Thr Pro Thr Gly Ala Thr Gly Asn Ile Thr Val Thr Trp Gln
            690                 695                 700
Asn
705

<210> SEQ ID NO 4
```

```
<211> LENGTH: 515
<212> TYPE: PRT
<213> ORGANISM: Bacillus flexus

<400> SEQUENCE: 4
```

| | | | | | | | | | | | | | | |
|---|---|---|---|---|---|---|---|---|---|---|---|---|---|---|
|Ala|Val|Asn|Gly|Gln|Ser|Phe|Asn|Ser|Asn|Tyr|Lys|Thr|Tyr|Leu|Met
1| | | |5| | | | |10| | | | |15| |

Ala Pro Leu Lys Lys Val Thr Glu Phe Thr Thr Trp Glu Ala Phe Glu
                20                  25                  30

Asn Asp Leu Arg Lys Ala Lys Gln Asn Gly Phe Tyr Ala Val Thr Val
             35                  40                  45

Asp Phe Trp Trp Gly Asp Met Glu Lys Asn Gly Asp Gln Gln Phe Asp
 50                  55                  60

Phe Ser Tyr Ala Gln Arg Phe Ala Gln Ala Ala Arg Asn Ala Gly Ile
 65                  70                  75                  80

Lys Met Val Pro Ile Ile Ser Thr His Gln Cys Gly Gly Asn Val Gly
                 85                  90                  95

Asp Asp Cys Asn Thr Pro Leu Pro Ser Trp Ile Trp Asn Thr Lys Thr
                100                 105                 110

Asp Asp Ser Leu Tyr Phe Lys Ser Glu Thr Gly Thr Val Asn Lys Glu
             115                 120                 125

Thr Val Asn Pro Leu Ala Thr Asp Val Ile Thr Lys Gln Tyr Gly Glu
130                 135                 140

Leu Tyr Thr Ala Phe Ala Gln Ala Leu Ala Pro Tyr Lys Asp Val Ile
145                 150                 155                 160

Pro Lys Val Tyr Leu Ser Gly Gly Pro Ala Gly Glu Leu Arg Tyr Pro
                165                 170                 175

Ser Tyr Thr Ala Ala Asp Gly Thr Gly Tyr Pro Ser Arg Gly Lys Phe
            180                 185                 190

Gln Ala Tyr Thr Asp Phe Ala Lys Ser Lys Phe Gln Met Trp Ala Val
         195                 200                 205

Asn Lys Tyr Gly Ser Leu Ala Gly Val Asn Gln Ala Trp Gly Leu Ser
    210                 215                 220

Leu Thr Ser Thr Ser Gln Ile Leu Pro Pro Ser Asp Gly Asn Gln Phe
225                 230                 235                 240

Leu Lys Asp Gly Tyr Asn Thr Asn Tyr Gly Lys Asp Phe Leu Glu Trp
                245                 250                 255

Tyr Gln Gly Val Leu Gln Asp His Ala Lys Arg Ile Gly Ala Leu Ala
            260                 265                 270

His Gln Ala Phe Asp Pro Val Phe Asn Val Pro Val Gly Ala Lys Ile
        275                 280                 285

Ala Gly Ile His Trp Gln Tyr Asn Asn Pro Thr Met Pro His Ala Ala
    290                 295                 300

Glu Lys Pro Ala Gly Tyr Asn Asn Tyr Ser Thr Leu Leu Asp Ser Phe
305                 310                 315                 320

Lys Thr Ala Lys Leu Asp Leu Thr Phe Thr Cys Leu Glu Met Val Asp
                325                 330                 335

Ser Gly Thr Tyr Pro Glu Tyr Ser Met Pro Lys Thr Leu Val Lys Glu
            340                 345                 350

Val Ala Ser Leu Ala Asn Ala Lys Gly Ile Val Leu Asn Gly Glu Asn
        355                 360                 365

Ala Leu Ser Ile Gly Ser Glu Glu Gln Tyr Lys Arg Ala Ala Glu Met
    370                 375                 380

Thr Phe Asn Tyr Asn Phe Ala Gly Phe Thr Leu Leu Arg Phe Tyr Asp

```
                385                 390                 395                 400
Val Ile Asn Asn Ser Thr Arg Met Ser Gln Phe Asn Gln His Leu Asn
                    405                 410                 415

Ile Lys Pro Val Ala Gln Thr Met Val Val Lys Asn Ala Pro Thr Ser
            420                 425                 430

Ser Gly Glu Ser Val Tyr Ile Val Gly Asp Arg Pro Glu Leu Gly Gln
        435                 440                 445

Trp Asp Thr Ile Ala Tyr Pro Ile Lys Leu Ser Tyr Asn Ser Thr Tyr
450                 455                 460

Gly Asp Trp Arg Gly Thr Val Asn Phe Pro Ala Asp Arg Ser Val Gln
465                 470                 475                 480

Phe Lys Ala Ile Ile Lys Arg Ser Asp Gly Ser Leu Lys Ser Trp Gln
                485                 490                 495

Pro Thr Gln Gln Tyr Trp Asn Val Pro Gly Thr Pro Thr Thr Tyr Thr
            500                 505                 510

Asn Asn Trp
        515

<210> SEQ ID NO 5
<211> LENGTH: 429
<212> TYPE: PRT
<213> ORGANISM: Pseudomonas saccharophila

<400> SEQUENCE: 5

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Asn Asp Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
        50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
210                 215                 220

Ser Glu Tyr Pro Ser Trp Asp Trp Arg Asn Thr Ala Ser Trp Gln Gln
225                 230                 235                 240
```

```
Ile Ile Lys Asp Trp Ser Asp Arg Ala Lys Cys Pro Val Phe Asp Phe
            245                 250                 255

Ala Leu Lys Glu Arg Met Gln Asn Gly Ser Val Ala Asp Trp Lys His
        260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425
```

<210> SEQ ID NO 6
<211> LENGTH: 2118
<212> TYPE: DNA
<213> ORGANISM: Artificial sequence
<220> FEATURE:
<223> OTHER INFORMATION: Synthetic construct

<400> SEQUENCE: 6

```
atgagatttc cttcaattttt tactacagtt ttattcgcag catcctccgc attagcttca      60
tcttcagcaa gcgttaaagg ggacgtcatc tatcagatca taatcgatag attctatgat     120
ggagatacaa caaacaataa cccagctaag agttatggtt tgtatgatcc tactaagagc     180
aaatggaaaa tgtactgggg tggtgattta gaaggtgtta gacaaaagct accataccctg    240
aagcagttag gcgtaaccac gatttggtta tctccagttt tagacaactt agacaccttg     300
gcaggaacag acaatacggg ttatcacggt tactggacaa gggactttaa gcaaattgag     360
gaacacttcg gtaattggac aacgttcgat acacttgtta acgatgctca tcagaacggc     420
atcaaggtta tagttgattt cgttcccaat catagcacac ccttcaaagc aaatgattcc     480
acgtttgctg aaggtggagc cttgtataac aatgggacct atatgggcaa ctactttgac     540
gacgctacaa aagggtactt ccatcacaat ggagacattt caaactggga cgatagatac     600
gaagcacaat ggaagaactt tacagatcct gctggattct cacttgccga cctgtcccaa     660
gagaatggaa ctattgctca gtatttgacc gatgctgctg ttcaactggt cgcacacggt     720
gcagatggcc ttcgtataga tgccgttaag cacttcaatt ctggatttc aaaaagcctg     780
gcagacaagc tataccaaaa gaaagacatc ttcttagtag gagaatggta tggagacgac     840
cctggtacgg caaatcacct agaaaaggtt agatatgcca ataactccgg tgtcaacgtc     900
ttagacttcg acttgaatac agtcattaga acgttttttg gtactttcac tcaaacaatg     960
tacgatctta caatatggtt aaaccagacg ggtaatgagt acaagtacaa agaaaacttg    1020
```

| | |
|---|---|
| attaccttca tagacaatca tgatatgtct agatttcttt ctgttaactc caacaaagcc | 1080 |
| aaccttcatc aagcattggc cttcattttg acttccaggg gtactccttc catttactac | 1140 |
| ggaacagagc aatacatggc tggtggtaac gaccectata acagaggcat gatgcctgct | 1200 |
| tttgatacga ctactactgc ctttaaggaa gtctccaccc tggctggttt gaggaggaac | 1260 |
| aatgctgcca tacaatatgg gacaacaact caaaggtgga tcaataacga tgtctacatc | 1320 |
| tatgagagga agttcttcaa tgacgttgtt cttgtagcca ttaacagaaa tactcagtca | 1380 |
| tcttatagta tttctggttt gcaaaccgct ctaccaaacg gatcatatgc cgactactta | 1440 |
| tctggtttgt taggtggcaa tggaatatca gtttcaaatg gcagtgtcgc atcctttacc | 1500 |
| ttggcacctg gtgccgtatc tgtatggcag tattcaacat ctgctagcgc acctcaaatt | 1560 |
| ggttcagttg ctcccaatat gggtattcca ggtaatgttg tgactatcga tggtaaaggg | 1620 |
| tttgggacga cacaaggaac cgttacattt ggtggcgtga cagccactgt gaaaagttgg | 1680 |
| acgtcaaata gaatcgaagt atatgtacca aacatggctg ccggtttgac agatgttaag | 1740 |
| gtcacagccg gtggtgtctc ctcaaacttg tattcctata catttttgtc tggaacccaa | 1800 |
| actagcgtgg tgtttactgt caaatctgct ccaccaacaa atctagggga caagatctac | 1860 |
| ttaactggga acattcccga attgggaaat tggagcacgg atacatctgg ggctgtcaac | 1920 |
| aatgcacaag gcccactatt agctcccaat taccccgact ggttctatgt tttctccgtt | 1980 |
| ccagctggta aaactattca gtttaagttc ttcatcaaaa gagccgatgg aacaatccag | 2040 |
| tgggagaacg ggtcaaatca tgtggctacg actccaacag gggctactgg caatatcacg | 2100 |
| gtcacttggc aaaactaa | 2118 |

<210> SEQ ID NO 7
<211> LENGTH: 2118
<212> TYPE: DNA
<213> ORGANISM: Artificial sequence
<220> FEATURE:
<223> OTHER INFORMATION: Synthetic construct

<400> SEQUENCE: 7

| | |
|---|---|
| atgagatttc cttcaatttt tactacagtt ttattcgcag catcctccgc attagcttca | 60 |
| tcttcagcaa gcgttaaagg ggacgtcatc tatcagatca taatcgatag attctatgat | 120 |
| ggagatacaa caaacaataa cccagctaag agttatggtt gtatgatcc tactaagagc | 180 |
| aaatggaaaa tgtactgggg tggtgattta gaaggtgtta gacaaaagct accatacctg | 240 |
| aagcagttag gcgtaaccac gatttggtta tctccagttt tagacaactt agacaccttg | 300 |
| gcaggaacag acaatacggg ttatcacggt tactggacaa gggactttaa gcaaattgag | 360 |
| gaacacttcg gtaattggac aacgttcgat acacttgtta acgatgctca tcagaacggc | 420 |
| atcaaggtta tagttgattt cgttcccaat catagcacac ccttcaaagc aaatgattcc | 480 |
| acgtttgctg aaggtggagc cttgtataac aatgggacct atatgggcaa ctactttgac | 540 |
| gacgctacaa aagggtactt ccatcacaat ggagacattt caaactggga cgatagatac | 600 |
| gaagcacaat ggaagaactt aacagatcct gctggattct cacttgccga cctgtcccaa | 660 |
| gagaatggaa ctattgctca gtatttgacc gatgctgctg ttcaactggt cgcacacggt | 720 |
| gcagatggcc ttcgtataga tgccgttaag cacttcaatt ctggattttc aaaaagcctg | 780 |
| gcagacaagc tataccaaaa gaaagacatc ttcttagtag agaatggta tggagatggg | 840 |
| cctggtacgg caaatcacct agaaaaggtt agatatgcca ataactccgg tgtcaacgtc | 900 |

-continued

```
ttagacttcg acttgaatcc tgtcattaga aacgttttg gtactttcac tcaaacaatg      960
tacgatctta acaatatggt aaaccagacg ggtaatgagt acaagtacaa agaaaacttg     1020
attaccttca tagacaatca tgatatgtct agatttcttt ctgttaactc caacaaagcc     1080
aaccttcatc aagcattggc cttcattttg acttccaggg gtactccttc catttactac     1140
ggaacagagc aatacatggc tggtggtaac gacccctata acagaggcat gatgcctgct     1200
tttgatacga ctactactgc ctttaaggaa gtctccaccc tggctggttt gaggaggaac     1260
aatgctgcca tacaatatgg gacaacaact caaaggtgga tcaataacga tgtctacatc     1320
tatgagagga agttcttcaa tgacgttgtt cttgtagcca ttaacagaaa tactcagtca     1380
tcttatagta tttctggttt gcaaaccgct ctaccaaacg gatcatatgc cgactactta     1440
tctggttttgt taggtggcaa tggaatatca gtttcaaatg gcagtgtcgc atcctttacc     1500
ttggcacctg gtgccgtatc tgtatggcag tattcaacat ctgctagcgc acctcaaatt     1560
ggttcagttg ctcccaatat gggtattcca ggtaatgttg tgactatcga tggtaaaggg     1620
tttgggacga cacaaggaac cgttacattt ggtggcgtga cagccactgt gaaaagttgg     1680
acgtcaaata gaatcgaagt atatgtacca aacatggctg ccggtttgac agatgttaag     1740
gtcacagccg gtggtgtctc ctcaaacttg tattcctata acattttgtc tggaacccaa     1800
actagcgtgg tgtttactgt caaatctgct ccaccaacaa atctagggga caagatctac     1860
ttaactggga acattcccga attgggaaat tggagcacgg atacatctgg ggctgtcaac     1920
aatgcacaag gcccactatt agctcccaat taccccgact ggttctatgt tttctccgtt     1980
ccagctggta aaactattca gtttaagttc ttcatcaaaa gagccgatgg aacaatccag     2040
tgggagaacg ggtcaaatca tgtggctacg actccaacag gggctactgg caatatcacg     2100
gtcacttggc aaaactaa                                                   2118
```

<210> SEQ ID NO 8
<211> LENGTH: 2118
<212> TYPE: DNA
<213> ORGANISM: Artificial sequence
<220> FEATURE:
<223> OTHER INFORMATION: Synthetic construct

<400> SEQUENCE: 8

```
atgagatttc cttcaattt tactacagtt ttattcgcag catcctccgc attagcttca       60
tcttcagcaa gcgttaaagg ggacgtcatc tatcagatca taatcgatag attctatgat      120
ggagatacaa caaacaataa cccagctaag tcctatggtt tgtatgatcc tactaagagc      180
aaatggaaaa tgtactgggg tggtgattta aaggtgttta gacaaaagct accatacctg      240
aagcagttag gcgtaaccac gatttggtta tctccagttt tagacaactt agacaccttg      300
gcaggaacag acaatacggg ttatcacggt tactggacaa gggactttaa gcaaattgag      360
gaacacttcg gtaattggac aacgttcgat acacttgtta acgatgctca tcagaacggc      420
atcaaggtta tagttgattt cgttcccaat catagcacac ccttcaaagc aaatgatagt      480
acgtttgctg aaggtggagc cttgtataac aatgggacct atatgggcaa ctactttgac      540
gacgctacaa aagggtactt ccatcacaat ggagacattt caaactggga cgatagatac      600
gaagcacaat ggaagaactt tacagatcct gctggatact cacttgccga cctgagtcaa      660
gagaatggaa ctattgctca gtatttgacc gatgctgctg ttcaactggt cgcacacggt      720
gcagatggcc ttcgtataga tgccgttaag cacttcaatt ctggattttc aaaaagcctg      780
gcagacaagc tataccaaaa gaaagacatc ttcttagtag gagaatggta tggagatggg      840
```

```
cctggtacgg caaatcacct agaaaaggtt agatatgcca ataacagtgg tgtcaacgtc    900
ttagacttcg acttgaatcc tgtcattaga aacgtttttg gtactttcac tcaaacaatg    960
tacgatctta acaatatggt aaaccagacg ggtaatgagt acaagtacaa agaaaacttg   1020
attaccttca tagacaatca tgatatgtct agatttcttt ctgttaactc caacaaagcc   1080
aaccttcatc aagcattggc cttcattttg actagtaggg gtactccttc catttactac   1140
ggaacagagc aatacatggc tggtggtaac gaccccctatt ccagaggcat gatgcctgct  1200
tttgatacga ctactactgc ctttaaggaa gtcagtaccc tggctggttt gaggaggaac   1260
aatgctgcca tacaatatgg gacaacaact caaaggtgga tcaataacga tgtctacatc   1320
tatgagagga agttcttcaa tgacgttgtt cttgtagcca ttaacagaaa tactcagtca   1380
tcttattcca tttctggttt gcaaaccgct ctaccaaacg gatcatatgc cgactactta   1440
tctggtttgt taggtggcaa tggaatatca gtttcaaatg gctccgtcgc aagttttacc   1500
ttggcacctg gtgccgtatc tgtatggcag tattcaacat ctgctagcgc acctcaaatt   1560
ggttcagttg ctcccaatat gggtattcca ggtaatgttg tgactatcga tggtaaaggg   1620
tttgggacga cacaaggaac cgttacattt ggtggcgtga cagccactgt gaaatcctgg   1680
acgtcaaata gaatcgaagt atatgtacca aacatggctg ccggtttgac agatgttaag   1740
gtcacagccg gtggtgtcag ttcaaacttg tattcctata acattttgtc tggaacccaa   1800
actagcgtgg tgtttactgt caaatctgct ccaccaacaa atctagggga caagatctac   1860
ttaactggga acattcccga attgggaaat tggagcacgg atacaagtgg ggctgtcaac   1920
aatgcacaag gcccactatt agctcccaat tacccccgact ggttctatgt tttcagtgtt  1980
ccagctggta aaactattca gtttaagttc ttcatcaaaa gagccgatgg aacaatccag   2040
tgggagaacg ggtcaaatca tgtggctacg actccaacag gggctactgg caatatcacg   2100
gtcacttggc aaaactaa                                                 2118
```

BAKERS'S YEAST EXPRESSING ANTI-STALING/FRESHNESS AMYLASES

CROSS-REFERENCE TO RELATED APPLICATIONS

This application is a 35 U.S.C. 371 national application of international application no. PCT/EP2018/073091 filed Aug. 28, 2018, which claims priority or the benefit under 35U.S.C. 119 of U.S. provisional application No. 62/551,318 filed Aug. 29, 2017, the contents of which are fully incorporated herein by reference.

REFERENCE TO A SEQUENCE LISTING

This application contains a Sequence Listing in computer readable form, which is incorporated herein by reference. The name of the file containing the Sequence Listing is SQ.txt, which was created on Jan. 28, 2021 and has 34.6 KB.

TECHNICAL FIELD

The present invention relates to a recombinant yeast cell expressing an anti-staling/freshness amylase, e.g., a maltogenic amylase for use in the baking area.

BACKGROUND

Maltogenic amylases (E.C. 3.2.1.133) are able to hydrolyze amylose and amylopectin forming maltose as the main reaction product. A maltogenic amylase is described in, e.g., EP 120 693 and is commercially available under the trade name Novamyl® (product of Novozymes A/S).

Novamyl is widely used in the baking industry as an anti-staling/freshness agent due to its ability to reduce retrogradation of starch/amylopectin. Variants of Novamyl are disclosed in, e.g., WO 99/43794.

Baker's yeast is normally used when producing breads, buns, etc.

It may be a substantial economic advantage if it is possible to make a baker's yeast that is capable of expressing anti-staling/freshness enzymes.

Certain baking applications may also benefit from continuous release of the anti-staling/freshness enzymes as opposed to adding a fixed amount of enzyme granulate/enzyme liquid during the mixing stage.

SUMMARY

The present inventors have found that it is possible to produce a recombinant yeast cell comprising a heterologous polynucleotide encoding a functional anti-staling/freshness amylase that may be used in baking.

In one embodiment, we claim a recombinant yeast cell comprising a heterologous polynucleotide encoding an anti-staling/freshness amylase selected from the group consisting of a maltogenic amylase (EC 3.2.1.133), a beta-amylase (EC 3.2.1.2), and a glucan 1,4-alpha-maltotetrahydrolase (EC 3.2.1.60).

In one embodiment, the heterologous polynucleotide encodes a maltogenic amylase having at least 70% sequence identity to amino acids 20-705 of SEQ ID NO:1.

In one embodiment, the heterologous polynucleotide encodes a maltogenic amylase selected from the group consisting of amino acids 20-705 of SEQ ID NO:1, amino acids 20-705 of SEQ ID NO:2, and amino acids 20-705 of SEQ ID NO:3.

In one embodiment, the heterologous polynucleotide encodes a beta-amylase polypeptide having at least 70% sequence identity to SEQ ID NO:4.

In one embodiment, the heterologous polynucleotide encodes a glucan 1,4-alpha-maltotetrahydrolase having at least 70% sequence identity to SEQ ID NO:5.

In one embodiment, the heterologous polynucleotide comprises a coding sequence having at least 70% sequence identity to SEQ ID NO: 6, SEQ ID NO:7, or SEQ ID NO:8.

In one embodiment, the recombinant yeast cell is a *Saccharomyces* cell.

In one embodiment, the recombinant yeast cell is a *Saccharomyces cerevisiae* cell.

In one embodiment, we claim a process for producing a dough, comprising adding a recombinant yeast cell comprising a heterologous polynucleotide encoding an anti-staling/freshness amylase selected from the group consisting of a maltogenic amylase (EC 3.2.1.133), a beta-amylase (EC 3.2.1.2), and a glucan 1,4-alpha-maltotetrahydrolase (EC 3.2.1.60) to dough ingredients and making the dough.

In one embodiment, a baked or a steamed product is made from the dough.

In one embodiment, an enzyme selected from the group consisting of amylase, glucanase, galactanase, mannanase, aminopeptidase, alpha-amylase, carboxypeptidase, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, phospholipase, mannosidase, oxidase, pectinolytic enzymes, peptidoglutaminase, peroxidase, phytase, glucose oxidase, polyphenoloxidase, proteolytic enzyme, ribonuclease, transglutaminase and xylanase is added to the dough.

In one embodiment, one of the dough ingredients is flour.

In one embodiment, the flour is selected from the group consisting of wheat, emmer, spelt, einkorn, barley, rye, oat, corn, sorghum, rice, millet, amaranth, *quinoa*, and cassava and any combinations thereof.

In one embodiment, we claim the use of the recombinant yeast cell according to present invention in dough making.

In one embodiment, the recombinant yeast cell is used as a Baker's yeast.

Definitions

Unless defined otherwise or clearly indicated by context, all technical and scientific terms used herein have the same meaning as commonly understood by one of ordinary skill in the art.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by processes known in the art, e.g., by directed homologous recombination (see *Processes in Yeast Genetics* (1997 edition), Adams, Gottschling, Kaiser, and Stems, Cold Spring Harbor Press (1998)).

Endogenous gene: The term "endogenous gene" means a gene that is native to the referenced host cell. "Endogenous gene expression" means expression of an endogenous gene.

Expression: The term "expression" includes any step involved in the production of the polypeptide including, but not limited to, transcription, post-transcriptional modification, translation, post-translational modification, and secretion. Expression can be measured, for example, to detect increased expression by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

Host cell: The term "host cell" means any cell type that is susceptible to transformation, transfection, transduction, and the like with a nucleic acid construct or expression vector. The term "host cell" encompasses any progeny of a parent cell that is not identical to the parent cell due to mutations that occur during replication. The term "recombinant cell" is defined herein as a non-naturally occurring host cell comprising one or more (e.g., two, several) heterologous polynucleotides.

Improved property: When the yeast comprising the anti-staling/freshness amylase according to the invention, is incorporated into a flour and/or a dough in effective amounts, one or more properties are improved compared to a flour and/or a dough in which the yeast comprising the anti-staling/freshness amylase is not added.

The improved property may be determined by comparison of a dough and/or a baked product prepared with addition of the yeast comprising a heterologous polynucleotide encoding the anti-staling/freshness amylase of the present invention, and a yeast without the heterologous polynucleotide encoding the anti-staling/freshness amylase of the present invention in accordance with the methods described below.

Organoleptic qualities may be evaluated using procedures well established in the baking industry, and may include, for example, the use of a trained sensory panel.

Improved extensibility: The term "improved extensibility of the dough" is defined herein as the property of dough that can be subjected to increased stretching without rupture.

Increased strength: The term "increased strength of the dough" is defined herein as the property of dough that has generally more elastic properties and/or requires more work input to mould and shape.

Increased elasticity: The term "increased elasticity of the dough" is defined herein as the property of dough which has a higher tendency to regain its original shape after being subjected to a certain physical strain.

Increased stability of the dough: The term "increased stability of the dough" is defined herein as the property of dough that is less susceptible to mechanical abuse thus better maintaining its shape and volume and is evaluated by the ratio of height:width of a cross section of a loaf after normal and/or extended proof.

Reduced stickiness of the dough: The term "reduced stickiness of the dough" is defined herein as the property of a dough that has less tendency to adhere to surfaces, e.g., in the dough production machinery, and is either evaluated empirically by the skilled test baker or measured by use of a texture analyzer (e.g., TAXT2) as known in the art.

Improved machine ability: The term "improved machine ability of the dough" is defined herein as the property of a dough that is generally less sticky and/or more firm and/or more elastic.

Increased volume of the dough/the baked product: The term "increased volume of the dough/baked product" is measured as the volume of a dough or the volume of a given loaf of bread. The volume may, e.g., be determined by the rape seed displacement method, or by a skilled baker, or by using, e.g., a Volscan profiler 600.

Improved crumb structure of the baked product: The term "improved crumb structure of the baked product" is defined herein as the property of a baked product regarding crumb uniformity, cell wall thickness, and the size of the individual gas cells pores on the slice of bread.

The crumb structure of the baked product is usually evaluated visually by the baker or by digital image analysis as known in the art (e.g., C-cell, Calibre Control International Ltd, Appleton, Warrington, UK).

Improved anti-staling/freshness of the baked product: The term "improved anti-staling/freshness of the baked product" is the opposite of "firmness" and is defined herein as the property of a baked product that is more easily compressed and is evaluated either empirically by the skilled test baker or measured by use of a texture analyzer (e.g., TAXT2 or TA.XT Plus from Stable Micro Systems Ltd, Surrey, UK) as known in the art.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs expression of the coding sequence.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, *J. Mol. Biol.* 1970, 48, 443-453) as implemented in the Needle program of the EMBOSS package (EMBOSS: The European Molecular Biology Open Software Suite, Rice et al., *Trends Genet* 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970) as implemented in the Needle program of the EMBOSS package (EMBOSS: The European Molecular Biology Open Software Suite, Rice et al., 2000), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Referenced Sequence−Total Number of Gaps in Alignment)

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the process of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments.

DETAILED DESCRIPTION

Anti-Staling/Freshness Amylases

The Applicant has found that it is possible to express a functional anti-staling/freshness amylase in a yeast cell, such as a *Saccharomyces cerevisiae* yeast cell, and use this recombinant yeast cell in baking.

Accordingly, in one aspect a recombinant yeast cell comprising a heterologous polynucleotide encoding an anti-staling/freshness amylase is claimed, wherein anti-staling/freshness enzyme is selected from the group consisting of a maltogenic amylase (EC 3.2.1.133), a beta-amylase (EC 3.2.1.2), and a glucan 1,4-alpha-maltotetrahydrolase (EC 3.2.1.60).

In one embodiment, the maltogenic amylase comprises or consists of the amino acids 20-705 of SEQ ID NO: 1.

In another embodiment, the maltogenic amylase is a fragment of SEQ ID NO: 1 (e.g., wherein the fragment has maltogenic amylase activity). In one embodiment, the number of amino acid residues in the fragment is at least 75%, e.g., at least 80%, 85%, 90%, or 95% of the number of amino acid residues in the maltogenic amylase of SEQ ID NO: 1.

The maltogenic amylase may be a variant of the maltogenic amylase of SEQ ID NO: 1. In one embodiment, the maltogenic amylase has at least 70%, e.g., at least 75%, 80%, 85%, 90%, 91%, 92%, 93%, 94%, 95%, 96%, 97%, 98%, 99%, or 100% sequence identity to amino acids 20-705 of SEQ ID NO: 1.

In one embodiment, the maltogenic amylase comprises or consists of the amino acids 20-705 of SEQ ID NO: 2 or comprises or consists of the amino acids 20-705 of SEQ ID NO:3.

In one embodiment, the maltogenic amylase sequence differs by no more than ten amino acids, e.g., by no more than five amino acids, by no more than four amino acids, by no more than three amino acids, by no more than two amino acids, or by one amino acid from amino acid sequence of maltogenic amylase of SEQ ID NO: 1. In one embodiment, the maltogenic amylase has an amino acid substitution, deletion, and/or insertion of one or more (e.g., two, several) of amino acid sequence of the of SEQ ID NO: 1. In some embodiments, the total number of amino acid substitutions, deletions and/or insertions is not more than 10, e.g., not more than 9, 8, 7, 6, 5, 4, 3, 2, or 1.

In one embodiment, the beta-amylase comprises or consists of the amino acid sequence of SEQ ID NO: 4. In another embodiment, the beta-amylase is a fragment of SEQ ID NO: 4 (e.g., wherein the fragment has beta-amylase activity). In one embodiment, the number of amino acid residues in the fragment is at least 75%, e.g., at least 80%, 85%, 90%, or 95% of the number of amino acid residues in the beta-amylase of SEQ ID NO: 4.

The beta-amylase may be a variant of the beta-amylase of SEQ ID NO: 4. In one embodiment, the beta-amylase has at least 70%, e.g., at least 75%, 80%, 85%, 90%, 91%, 92%, 93%, 94%, 95%, 96%, 97%, 98%, 99%, or 100% sequence identity to the beta-amylase of SEQ ID NO: 4.

In one embodiment, the beta-amylase sequence differs by no more than ten amino acids, e.g., by no more than five amino acids, by no more than four amino acids, by no more than three amino acids, by no more than two amino acids, or by one amino acid from amino acid sequence of beta-amylase of SEQ ID NO: 4. In one embodiment, the beta-amylase has an amino acid substitution, deletion, and/or insertion of one or more (e.g., two, several) of amino acid sequence of the of SEQ ID NO: 4. In some embodiments, the total number of amino acid substitutions, deletions and/or insertions is not more than 10, e.g., not more than 9, 8, 7, 6, 5, 4, 3, 2, or 1.

In one embodiment, the glucan 1,4-alpha-maltotetrahydrolase comprises or consists of the amino acid sequence of SEQ ID NO: 5. In another embodiment, the glucan 1,4-alpha-maltotetrahydrolase is a fragment of SEQ ID NO: 5 (e.g., wherein the fragment has maltotetraohydrolase activity). In one embodiment, the number of amino acid residues in the fragment is at least 75%, e.g., at least 80%, 85%, 90%, or 95% of the number of amino acid residues in the maltogenic amylase of SEQ ID NO: 5.

The glucan 1,4-alpha-maltotetrahydrolase may be a variant of the glucan 1,4-alpha-maltotetrahydrolase of SEQ ID NO: 5. In one embodiment, the glucan 1,4-alpha-maltotetrahydrolase has at least 70%, e.g., at least 75%, 80%, 85%, 90%, 91%, 92%, 93%, 94%, 95%, 96%, 97%, 98%, 99%, or 100% sequence identity to the glucan 1,4-alpha-maltotetrahydrolase of SEQ ID NO: 5.

In one embodiment, the glucan 1,4-alpha-maltotetrahydrolase sequence differs by no more than ten amino acids, e.g., by no more than five amino acids, by no more than four amino acids, by no more than three amino acids, by no more than two amino acids, or by one amino acid from amino acid sequence of glucan 1,4-alpha-maltotetrahydrolase of SEQ ID NO: 5. In one embodiment, the glucan 1,4-alpha-maltotetrahydrolase has an amino acid substitution, deletion, and/or insertion of one or more (e.g., two, several) of amino acid sequence of the of SEQ ID NO: 5. In some embodiments, the total number of amino acid substitutions, deletions and/or insertions is not more than 10, e.g., not more than 9, 8, 7, 6, 5, 4, 3, 2, or 1.

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the anti-staling/freshness amylase, alter the substrate specificity, change the pH optimum, and the like.

Essential amino acids can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for activity to identify amino acid residues that are critical to the activity of the molecule. See also, Hilton et al., 1996, J. Biol. Chem. 271: 4699-4708. The active site or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64.

Guidance on the structure-activity relationship of anti-staling/freshness amylases described herein can be inferred from numerous crystal structures analyzed and known in the art. Additional guidance on the structure-activity relationship of anti-staling/freshness amylases can be determined using multiple sequence alignment (MSA) techniques well-known in the art. Such alignments aid the skilled artisan to determine potentially relevant domains (e.g., binding domains or catalytic domains), as well as which amino acid residues are conserved and not conserved among the different anti-staling/freshness amylase sequences. It is appreciated in the art that changing an amino acid that is conserved at a particular position between disclosed polypeptides will more likely result in a change in biological activity (Bowie et al., 1990, Science 247: 1306-1310: "Residues that are directly involved in protein functions such as binding or catalysis will certainly be among the most conserved"). In contrast, substituting an amino acid that is not highly conserved among the polypeptides will not likely or significantly alter the biological activity.

Single or multiple amino acid substitutions, deletions, and/or insertions can be made and tested using known processes of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other processes that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling processes can be combined with high-throughput, automated screening processes to detect activity of cloned, mutagenized polypeptides expressed by host cells (Ness et al., 1999, Nature Biotechnology 17: 893-896). Mutagenized DNA molecules that encode active anti-staling/freshness amylases can be recovered from the host cells and rapidly sequenced using standard processes in the art. These processes allow the rapid determination of the importance of individual amino acid residues in a polypeptide.

Polynucleotides Encoding Anti-Staling/Freshness Amylases

The heterologous polynucleotide encoding the anti-staling/freshness amylase may comprise a coding sequence having at least 70%, e.g., at least 75%, at least 80%, at least 85%, at least 90%, at least 95%, at least 96%, at least 97%, at least 98%, at least 99%, or 100% sequence identity to nucleotides of SEQ ID NO: 6, SEQ ID NO: 7, or SEQ ID NO: 8.

In one embodiment, the heterologous polynucleotide encoding the anti-staling/freshness amylase comprises or consists of the coding sequence of SEQ ID NO: 21. In another embodiment, the heterologous polynucleotide encoding the anti-staling/freshness amylase comprises a subsequence of the coding sequence of SEQ ID NO: 6, SEQ ID NO: 7, or SEQ ID NO: 8. In another embodiment, the number of nucleotides residues in the coding subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for a particular host cell.

The polynucleotide coding sequence of SEQ ID NO: 6, SEQ ID NO: 7, or SEQ ID NO: 8, or a subsequence thereof, may be used to design nucleic acid probes to identify and clone DNA encoding an anti-staling/freshness amylase from strains of different genera or species according to processes well known in the art.

In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 6, SEQ ID NO: 7, or SEQ ID NO: 8, or a subsequence thereof, the carrier material is used in a Southern blot.

In one embodiment, the nucleic acid probe is a polynucleotide comprising SEQ ID NO: 6, SEQ ID NO: 7, or SEQ ID NO: 8; or a subsequence thereof. In another embodiment, the nucleic acid probe is a polynucleotide that encodes the anti-staling/freshness amylase of SEQ ID NO: 6, SEQ ID NO: 7, or SEQ ID NO: 8; or a fragment thereof.

For purposes of the probes described above, hybridization indicates that the polynucleotide hybridizes to a labeled nucleic acid probe, or the full-length complementary strand thereof, or a subsequence of the foregoing; under very low to very high stringency conditions. Molecules to which the nucleic acid probe hybridizes under these conditions can be detected using, for example, X-ray film.

In one embodiment, the anti-staling/freshness amylase is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 6, SEQ ID NO: 7, or SEQ ID NO: 8. (Sambrook et al., 1989, Molecular Cloning, A Laboratory Manual, 2d edition, Cold Spring Harbor, New York).

The anti-staling/freshness amylase may be obtained from microorganisms of any suitable genus, including those readily available within the UniProtKB database (www.uniprot.org).

The anti-staling/freshness amylase may be a bacterial anti-staling/freshness amylase. For example, the anti-staling/freshness amylase may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* anti-staling/freshness amylase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* anti-staling/freshness amylase.

The anti-staling/freshness amylase may be a fungal anti-staling/freshness amylase. For example, the anti-staling/freshness amylase may be a yeast anti-staling/freshness amylase such as a *Candida, Kluyveromyces, Pichia, Saccharomyces, Schizosaccharomyces, Yarrowia* or *Issatchenkia* anti-staling/freshness amylase; or a filamentous fungal anti-staling/freshness amylase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* anti-staling/freshness amylase.

It will be understood that for the afore mentioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The anti-staling/freshness amylase may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding an anti-staling/freshness amylase may then be derived by similarly screening a genomic or cDNA library of another microorganism or mixed DNA sample.

Once a polynucleotide encoding an anti-staling/freshness amylase has been detected with a suitable probe as described herein, the sequence may be isolated or cloned by utilizing techniques that are known to those of ordinary skill in the art. Techniques used to isolate or clone polynucleotides encoding anti-staling/freshness amylase include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shares structural features. See, e.g., Innis et al., 1990, *PCR: A Guide to Processes and Application*, Academic Press, New York. Other nucleic acid amplification procedures such as ligase chain reaction (LCR), ligated activated transcription (LAT) and nucleotide sequence-based amplification (NASBA) may be used.

The anti-staling/freshness amylase may be a fused polypeptide or cleavable fusion polypeptide in which another polypeptide is fused at the N-terminus or the C-terminus of the anti-staling/freshness amylase.

Hosts Cells and Recombinant Processes

The yeast host cells for preparing the recombinant cells described herein can be from any suitable yeast host, such as a *Saccharomyces* cell. Preferably, the yeast cell is a *Saccharomyces cerevisiae* cell. Suitable cells can, for example, be derived from commercially available strains such as polyploid or aneuploid industrial strains, including but not limited to those from Baker's Best Yeast, Baker's Compressed Yeast, Baker's Dry Yeast etc. (commercially available as, e.g., Fleischmann's Yeast).

Other useful yeast strains are available from biological depositories such as the American Type Culture Collection (ATCC) or the Deutsche Sammlung von Mikroorganismen und Zellkulturen GmbH (DSMZ).

The recombinant cells described herein may utilize expression vectors comprising the coding sequence of one or more (e.g., two, several) heterologous genes linked to one or more control sequences that direct expression in a suitable cell under conditions compatible with the control sequence (s). Such expression vectors may be used in any of the cells and processes described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA processes are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the heterologous polynucleotide encoding the anti-staling/freshness amylase is operably linked to a promoter foreign to the polynucleotide. The promoters may be identical to or share a high degree of sequence identity (e.g., at least about 80%, at least about 85%, at least about 90%, at least about 95%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., *S. cerevisiae* 3-phosphoglycerate kinase or *I. orientalis* 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or *I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15: 5983-5990.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art.

Dough

In one aspect, the invention discloses a method for preparing dough or a baked product prepared from the dough which method comprises incorporating into the dough a recombinant yeast cell comprising a heterologous polynucleotide encoding an anti-staling/freshness amylase according to the invention.

In another aspect, the invention provides dough comprising flour, water, and an effective amount of a recombinant yeast cell comprising a heterologous polynucleotide encoding an anti-staling/freshness amylase according to the present invention.

The present invention also relates to methods for preparing a dough or a baked product comprising incorporating into the dough an effective amount of a recombinant yeast cell comprising a heterologous polynucleotide encoding an anti-staling/freshness amylase which improves one or more properties of the dough or the baked product obtained from the dough relative to a dough or a baked product in which the recombinant yeast cell comprising a heterologous polynucleotide encoding an anti-staling/freshness amylase is not incorporated.

The phrase "incorporating into the dough" is defined herein as adding the recombinant yeast cell comprising a heterologous polynucleotide encoding an anti-staling/freshness amylase according to the invention to the dough, to any ingredient from which the dough is to be made, and/or to any mixture of dough ingredients from which the dough is to be made.

The recombinant yeast cell comprising a heterologous polynucleotide encoding an anti-staling/freshness amylase is added to the ingredients of dough that may be kneaded and baked to make the baked product using methods well known in the art.

The term "effective amount" is defined herein as an amount of the recombinant yeast cell comprising a heterologous polynucleotide encoding an anti-staling/freshness amylase according to the invention that is sufficient for providing a measurable effect on at least one property of interest of the dough and/or baked product.

The term "dough" is defined herein as a mixture of flour and other ingredients firm enough to knead or roll. In the context of the present invention, batters are encompassed in the term "dough".

The dough of the invention may comprise flour derived from any cereal grain or other sources, including wheat, emmer, spelt, einkorn, barley, rye, oat, corn, sorghum, rice, millet, amaranth, *quinoa*, and cassava, and any combinations thereof.

The dough may also comprise other conventional dough ingredients, e.g., proteins, such as milk powder, gluten, and soy; eggs (either whole eggs, egg yolks, or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate, or calcium sulfate, and/or an emulsifier.

The dough may comprise fat (triglyceride) such as granulated fat or shortening.

The dough of the invention may be fresh, frozen or par-baked (pre-baked).

The dough of the invention is leavened dough or dough to be subjected to leavening.

Emulsifiers

For some applications, an emulsifier is not needed, but for other applications an emulsifier may be needed.

A suitable emulsifier for use in the present invention is preferably an emulsifier selected from the group consisting of diacetyl tartaric acid esters of monoglycerides (DATEM), sodium stearoyl lactylate (SSL), calcium stearoyl lactylate (CSL), ethoxylated mono- and diglycerides (EMG), distilled monoglycerides (DMG), polysorbates (PS), and succinylated monoglycerides (SMG).

Additional Enzymes

Optionally, one or more additional enzymes such as aminopeptidase, amylase, alpha-amylase, maltogenic amylase, beta-amylase, carboxypeptidase, catalase, chitinase, cutinase, cyclodextrin glycosyltransferase, deoxyribonuclease, esterase, galactanase, glucanase, alpha-galactosidase, beta-galactosidase, glucoamylase, alpha-glucosidase, beta-glucosidase, haloperoxidase, invertase, laccase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and/or xylanase may be used together with the recombinant yeast cell comprising a heterologous polynucleotide encoding an anti-staling/freshness amylase according to the present invention.

The glucoamylase for use in the present invention include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949).

The added amylase may be added to the dough on top of the amylase produced by the recombinant yeast cell according to the present invention. The amylase may be fungal or bacterial, e.g., a maltogenic amylase, a beta-amylase, or a fungal alpha-amylase, e.g., from *A. oryzae*.

Suitable commercial maltogenic alpha-amylases include NOVAMYL, OPTICAKE 50 BG, and OPTICAKE 3D (available from Novozymes A/S). Suitable commercial fungal alpha-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes A/S).

The amylase may also be an amylase (glucan 1,4-alpha-maltotetrahydrolase) from, e.g., *Pseudomonas*, such as any of the amylases disclosed in WO1999/050399, WO2004/111217, or WO2005/003339; e.g., G4™/G+™ available from DuPont.

The glucose oxidase may be a fungal glucose oxidase, in particular an *Aspergillus niger* glucose oxidase (such as GLUZYME®, available from Novozymes A/S).

The hemicellulase may be a pentosanase, e.g., a xylanase which may be of microbial origin, e.g., derived from a bacterium or fungus, such as a strain of *Aspergillus*, in particular of *A. aculeatus, A. niger, A. awamori*, or *A. tubigensis*, from a strain of *Trichoderma*, e.g., *T. reesei*, or from a strain of *Humicola*, e.g., *H. insolens*.

Suitable commercially available xylanase preparations for use in the present invention include PANZEA BG, PENTOPAN MONO BG and PENTOPAN 500 BG (available from Novozymes A/S), GRINDAMYL POWERBAKE (available from DuPont), and BAKEZYME BXP 5000 and BAKEZYME BXP 5001 (available from DSM).

The protease may be from *Bacillus*, e.g., *B. amyloliquefaciens* or from *Thermus aquaticus*.

Baked Product

The dough of the invention may be used for any kind of steamed or baked product prepared from dough, either of a white, light or dark type.

Examples are bread (in particular white, whole-meal or rye bread), typically in the form of loaves or rolls, bread, pita bread, tortillas, cakes, pancakes, biscuits, wafers, cookies, pie crusts, steamed bread, pizza and the like.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description.

The following examples are offered to illustrate certain aspects of the present invention, but not in any way intended to limit the scope of the invention as claimed.

EXAMPLES

Example 1

Construction of Plasmid Vectors Expressing an Anti-Staling/Freshness Amylase

Expression cassettes for the desired anti-staling/freshness amylases were targeted to the X-2 integration sites as described in Mikkelsen et al. (Metabolic Engineering v14 (2012) pp 104-111).

Two plasmids employing a split-marker approach were used for each integration event, each containing an expression cassette and approximately two-thirds of a dominant selection marker. The left-hand plasmid contained 5' flanking DNA homologous to the X-2 integration site, the *S. cerevisiae* TEF2 promoter driving expression of the gene of interest codon-optimized for expression in *S. cerevisiae*, the *S. cerevisiae* ADH3 terminator, a loxP site, and the 5' two-thirds of a dominant selection marker under control of the *Ashbya gossypii* TEF1 promoter. The right-hand plasmid contains the 3' two-thirds of the dominant selection marker with the *Ashbya gossypii* TEF1 terminator, a loxP site, an expression cassette in the reverse orientation relative to the dominant selection marker composed of the *S. cerevisiae* HXT7 promoter driving expression of the gene of interest codon-optimized for expression in *S. cerevisiae* with the *S. cerevisiae* PMA1 terminator, and 3' flanking DNA homologous to the X-2 integration site. The plasmids used for the strain construction are shown in Table 1 below:

TABLE 1

| Plasmid name | left- or right-hand | marker | SEQ ID |
|---|---|---|---|
| pMHCT379 | left | kanamycin | 1 |
| pMHCT380 | left | kanamycin | 2 |
| pMHCT381 | left | kanamycin | 3 |
| pMHCT384 | right | kanamycin | 1 |
| pMHCT385 | right | kanamycin | 2 |
| pMHCT386 | right | kanamycin | 3 |
| pMHCT387 | left | nourseothricin | 1 |
| pMHCT388 | left | nourseothricin | 2 |
| pMHCT389 | left | nourseothricin | 3 |
| pMHCT390 | right | nourseothricin | 1 |
| pMHCT391 | right | nourseothricin | 2 |
| pMHCT392 | right | nourseothricin | 3 |

Example 2

Construction of Recombinant Yeast Cells Expressing an Anti-Staling/Freshness Amylase Expression cassettes for the desired anti-staling/freshness amylase were targeted to the X-2 integration site of *S. cerevisiae* strain in a commercially available Fleischmann yeast using lithium acetate transformation (Gietz D, St. Jean A, Woods R, Schiestl R (1991) Improved method for high efficiency transformation of intact yeast cells. Nucleic Acids Research 20 (6) 1425).

Linearized DNAs corresponding to left- and right-hand expression cassettes with the kanamycin marker and linearized DNAs corresponding to left- and right-hand expression cassettes with the nourseothricin marker were simultaneously transformed into Fleischmann yeast and transformants resistant to both kanamycin and nourseothricin were selected, followed by PCR screening to confirm the desired integration events.

The antibiotic markers present in the above created strains are flanked by loxP sites. These intermediate strains were transformed with plasmid pFYD80 that includes a gene encoding the CRE recombinase, a site-specific enzyme that facilitates recombination between neighboring loxP sites (Güldener U, Heinisch J, Köhler G J, Voss D, Hegemann J H (2002) A second set of loxP marker cassettes for Cre-mediated multiple gene knockouts in budding yeast. Nucl Acids Res 30: e23).

Plasmid pFYD80 is maintained as a non-integrative, free replicating molecule. This approach enables the specific excision of both selective markers. The intermediate strains were transformed with plasmid pFYD80, and transformants were selected on plates containing zeocin. Zeocin resistance is encoded in pFYD80. Subsequently, screening for transformants that have lost nourseothricin and kanamycin resistance was performed. Sensitive strains were grown in YPD liquid until loss of pFYD80 plasmid was obtained.

Following this protocol, strain "Baker's yeast expressing SEQ ID NO:1" was selected and shown to be sensitive to zeocin, kanamycin, and nourseothricin. Strain "Baker's yeast expressing SEQ ID NO:1" is derived from *S. cerevisiae* strain Fleischmann yeast and expresses SEQ ID NO:1 from the X-2 integration site, one copy under control of the TEF2 promoter and the other copy under control of the HXT7 promoter. Since Fleischmann yeast is a tetraploid, two of the four X-2 chromosomal loci contain this tandem expression cassette, while the remaining two copies of X-2 remain wild-type.

Following this protocol, strain "Baker's yeast expressing SEQ ID NO:2" was selected and shown to be sensitive to zeocin, kanamycin, and nourseothricin. Strain "Baker's yeast expressing SEQ ID NO:2" is derived from *S. cerevisiae* strain Fleischmann yeast and expresses SEQ ID NO:2 from the X-2 integration site, one copy under control of the TEF2 promoter and the other copy under control of the HXT7 promoter. Since Fleischmann yeast is a tetraploid, two of the four X-2 chromosomal loci contain this tandem expression cassette, while the remaining two copies of X-2 remain wild-type.

Following this protocol, strain "Baker's yeast expressing SEQ ID NO: 3" was selected and shown to be sensitive to zeocin, kanamycin, and nourseothricin. Strain "Baker's yeast expressing SEQ ID NO: 3" is derived from *S. cerevisiae* strain Fleischmann yeast and expresses SEQ ID NO:3 from the X-2 integration site, one copy under control of the TEF2 promoter and the other copy under control of the HXT7 promoter. Since Fleischmann yeast is a tetraploid, two of the four X-2 chromosomal loci contain this tandem expression cassette, while the remaining two copies of X-2 remain wild-type.

Example 3

Baking Test with Baker's Yeast Expressing an Anti-Staling/Freshness Amylase

The ability of three yeast samples expressing anti-staling/freshness amylases to provide leavening and freshness was tested in a baking experiment employing bread samples based on 16 g dough pieces.

The baking experiment included the following four yeast samples:
1) Baker's yeast (Control-Fleischmann yeast)
2) Baker's yeast expressing SEQ ID NO:2 (made according to Example 2)
3) Baker's yeast expressing SEQ ID NO: 3 (made according to Example 2)
4) Baker's yeast expressing SEQ ID NO:1 (made according to Example 2)

Additionally, a benchmark of Novamyl 10000 BG (50 ppm, based on flour) was made.

The leavening ability of the yeast samples was verified by comparing volume of bread prepared with yeast with volume of bread prepared without yeast.

Mini-bread was prepared from the following ingredients:

| | |
|---|---|
| Standard wheat flour (Kolibri, Meneba BV, Rotterdam, Holland) | 100.0 g |
| Water | 58.5 g |
| Standard baker's yeast | 5.0 g |
| Salt | 1.5 g |
| Sugar | 1.5 g |
| Ascorbic acid | 4 mg |

Water content of the different yeast preparations was not identical which is why yeast was dosed on dry matter.

The dry matter of the yeast preparations was determined by placing approximately 500 mg yeast preparation on tarred aluminium trays in an oven (106° C.) over night. Dry matter of commercial baker's yeast contained approximately 31% dry matter, and all samples were dosed to equal 5 g yeast with this dry matter content.

Yeast expressing anti-staling/freshness amylase had lower dry matter compared to commercial baker's yeast which is why more yeast was added to ensure equal dry matter addition. The additional water added from the yeast preparations expressing freshness amylases were compensated by adding less water to the recipe.

Dough was prepared by mixing the ingredients for 4 minutes using a Model 325 gram Swanson pin mixer (National Manufacturing, TMG. Co. Lincoln, NE, US).

After mixing, dough was divided in 9 dough pieces of 16 g. Each dough piece was placed in closed pans (cylindrical pan, diameter 52 mm and height 30 mm). Dough was proofed for 55 min at 36° C. and 80% relative humidity and subsequently baked for 12 min at 210° C. After baking, the mini-bread samples were cooled and packed with nitrogen gas in sealed plastic bags.

On day 1, 3, and 8 after baking, the top of the mini-bread was removed with a knife and a cutting-box leaving 2 cm bread sample was obtained.

Crumb hardness was evaluated using a TA.XT plus Texture Analyzer (Stable Micro Systems, Surrey, UK) equipped with a spherical probe (25.4 mm diameter).

The bread sample was compressed 40% of the original height at a speed of 1.7 mm/s. Crumb hardness in grams at 25% compression was used to characterize the bread crumb hardness.

The leavening ability of the yeast samples were verified because all yeast-containing samples filled out the closed pan (63.7 mL) as opposed to dough prepared without yeast which had a volume after baking of approximately 15 mL.

Table 2 below shows crumb hardness as function of storage time of the three yeast preparations expressing anti-staling/freshness amylases. The table also includes hardness development for bread prepared with yeast not expressing anti-staling/freshness amylases (Control), and bread prepared with yeast not expressing anti-staling/freshness amylases but added commercial anti-staling/freshness amylase (Control+50 ppm Novamyl 10000BG).

TABLE 2

Crumb hardness (g) after 1, 3, and 8 days of storage

| | Day 1 | Day 3 | Day 8 |
|---|---|---|---|
| Control | 190 | 532 | 693 |
| Control + Novamyl 10000BG (50 ppm based on flour) | 108 | 283 | 346 |
| Yeast expressing SEQ ID NO: 2 | 146 | 361 | 598 |
| Yeast expressing SEQ ID NO: 3 | 146 | 435 | 693 |
| Yeast expressing SEQ ID NO: 1 | 146 | 486 | 770 |

It can be seen from Table 2 that the lowest increase in crumb hardness over time was observed for bread added commercial enzyme granulate (best anti-staling/freshness effect).

Yeast expressing SEQ ID NO:2 caused an anti-staling/freshness effect in between the Control and the "Control added Novamyl 10000BG".

Yeast expressing SEQ ID NO: 3 and SEQ ID NO:1 caused lower crumb hardness on day 3, while no differences appeared to exist between these two samples and the Control on Day 8.

Example 4

Baker's Yeast Expressing an Anti-Staling/Freshness Amylase in a Sponge and Dough Baking Test The yeast strains used in Example 3 were used in a sponge and dough baking trial:
Baker's yeast (Control-Fleischmann yeast)
Baker's yeast expressing SEQ ID NO: 2
Baker's yeast expressing SEQ ID NO: 3
Baker's yeast expressing SEQ ID NO:1
Additionally, a benchmark of Novamyl 10000 BG (50 ppm, based on flour) was made.

The baking trial was performed in 15 g scale in lidded pans.

The ingredients in the sponge (see Table 3) were placed in a 200 g pin mixer (National MFG Co, Lincoln, Nebraska, USA) and mixed into a sponge for 3 minutes at 90 rounds per minute. The sponge was placed in a large plastic container and proofed in a proofing cabinet for 3 h at 27° C. 75% rH.

The sponge was again placed in the 200 g pin mixer together with the ingredients of the dough (see Table 3) and mixed for 3 min at 90 rounds per minute into a dough. The dough was divided into nine 15 gram dough pieces that were rounded by hand into a roll and placed in a cylindrical pan with lid.

The lidded pan was placed on a continuous conveyor belt where the dough first was proofed for 63 min at 36° C. and 80% rH and baked for 10.5 min at 210° C.

After baking, the bread was removed from the pans and allowed to cool down for 10 min at room temperature after which they were placed in a sealed plastic bag and stored at room temperature until analyzed for crumb firmness.

Crumb firmness was evaluated using a TA.XT plus Texture Analyzer (Stable Micro Systems, Surrey, UK) equipped with a spherical probe (25.4 mm diameter).

The bread sample was compressed 40% of the original height at a speed of 1.7 mm/s. Crumb firmness in grams at 25% compression was used to characterize the bread crumb firmness.

TABLE 3

| Ingredients | Amount |
|---|---|
| Recipe | |
| Sponge | |
| Flour (Wigwam, US white flour) | 70 g |
| Water | 40.6 g |
| Soybean oil | 3 g |
| Yeast dry matter (See 4) | 2.15 g |
| Dough | |
| Flour (Wigwam, US white flour) | 30 g |
| Water | 20.4 g |
| Sugar | 5 g |
| Salt | 2 g |
| Calcium Propionate | 0.35 g |
| Ascorbic acid | 60 ppm |

Results

TABLE 4

Effect of different yeast strains on change in Firmness (g) measured with texture analyzer

| | Name | Day 1 | Day 3 | Day 7 |
|---|---|---|---|---|
| 1 | Control (Standard yeast - Fleischmann) | 93 | 398 | 506 |
| 2 | Standard yeast + Novamyl 10000 BG | 96 | 269 | 358 |
| 3 | Yeast expressing SEQ ID NO: 2 | 79 | 241 | 355 |
| 4 | Yeast expressing SEQ ID NO: 3 | 86 | 303 | 404 |
| 5 | Yeast expressing SEQ ID NO: 1 | 85 | 270 | 453 |

It can be seen from Table 4 that yeast expressing anti-staling/freshness enzymes were all better than the control; and the yeast expressing SEQ ID NO:2 was even better than adding 50 ppm Novamyl 10000 BG.

Example 5

Construction of Recombinant Yeast Cells Expressing Increased Amounts of Anti-Staling/Freshness Amylase To increase the amount of anti-staling/freshness amylase secreted from the yeast, the expression cassettes as described in Example 1 were re-transformed into the yeast strains constructed in Example 2. To do so, the expression cassettes for the desired anti-staling/freshness amylase were targeted to the X-2 integration site of strains "Baker's yeast expressing SEQ ID NO: 1", "Baker's yeast expressing SEQ ID NO: 2," and "Baker's yeast expressing SEQ ID NO: 3" using lithium acetate transformation (Gietz D, St. Jean A, Woods R, Schiestl R (1991) Improved method for high efficiency transformation of intact yeast cells. Nucleic Acids Research 20 (6) 1425). Linearized DNAs corresponding to left- and right-hand expression cassettes with the kanamycin marker and linearized DNAs corresponding to left- and right-hand expression cassettes with the nourseothricin marker were simultaneously transformed into the strains made in Example 2 with the matching poly-nucleotide. Transformants resistant to both kanamycin and nourseothricin were selected, followed by PCR screening. Since initial PCR screening for loss of the wild-type X-2 locus showed that all transformants still contained a wild-type locus, as second PCR primer set was used. These second PCR primers flanked the drug markers (nourseothricin and kanamycin). PCR results that showed both a larger band (the size expected when the drug markers were present) and a smaller band (the expected size after marker removal as described in Example 2) indicated that these isolates contained three chromosomes modified at the X-2 locus: one chromosome containing the marker-less expression cassette as made in Example 2, plus two additional modified chromosomes, one with the expression cassette containing the nourseothricin marker and one with the expression cassette containing the kanamycin marker. This lead to "Baker's yeast expressing SEQ ID NO: 1, three cassettes+markers", "Baker's yeast expressing SEQ ID NO: 2, three cassettes+markers," and "Baker's yeast expressing SEQ ID NO: 3, three cassettes+markers."

Following this protocol, strain "Baker's yeast expressing SEQ ID NO:3, three cassettes+markers" was selected and shown to be sensitive to zeocin, kanamycin, and nourseothricin. Strain "Baker's yeast expressing SEQ ID NO:3, three cassettes+markers" is derived from S. cerevisiae strain Fleischmann yeast and expresses SEQ ID NO:3 from the X-2 integration site, one copy under control of the TEF2 promoter and the other copy under control of the HXT7 promoter. Since Fleischmann yeast is a tetraploid, three of the four X-2 chromosomal loci contain this tandem expression cassette (two of which also contain drug markers), while the remaining one copy of X-2 remains wild-type.

The markers were removed from strains "Baker's yeast expressing SEQ ID NO: 1, three cassettes+markers" and "Baker's yeast expressing SEQ ID NO: 2, three cassettes+markers" using the pFYD80 plasmid as described in Example 2.

Following this protocol, strain "Baker's yeast expressing SEQ ID NO:1, three cassettes" was selected and shown to be sensitive to zeocin, kanamycin, and nourseothricin. Strain "Baker's yeast expressing SEQ ID NO:1" is derived from S. cerevisiae strain Fleischmann yeast and expresses SEQ ID NO:1 from the X-2 integration site, one copy under control of the TEF2 promoter and the other copy under control of the HXT7 promoter. Since Fleischmann yeast is a tetraploid, three of the four X-2 chromosomal loci contain this tandem expression cassette, while the remaining one copy of X-2 remains wild-type.

Following this protocol, strain "Baker's yeast expressing SEQ ID NO:2, three cassettes" was selected and shown to be sensitive to zeocin, kanamycin, and nourseothricin. Strain "Baker's yeast expressing SEQ ID NO:1" is derived from S. cerevisiae strain Fleischmann yeast and expresses SEQ ID NO:1 from the X-2 integration site, one copy under control of the TEF2 promoter and the other copy under control of the HXT7 promoter. Since Fleischmann yeast is a tetraploid, three of the four X-2 chromosomal loci contain this tandem expression cassette, while the remaining one copy of X-2 remains wild-type.

Example 6

Baker's Yeast Expressing an Increased Level of Anti-Staling/Freshness Amylase in a Sponge and Dough Baking Test Yeast strains constructed as described in Example 5 were used in a sponge and dough baking trial:
Baker's yeast (Control-Fleischmann yeast)
Baker's yeast expressing SEQ ID NO: 2, three cassettes
Baker's yeast expressing SEQ ID NO: 1, three cassettes
Baker's yeast expressing SEQ ID NO: 3, three cassettes+markers Additionally, a benchmark of Novamyl 10000 BG (50 ppm, based on flour) was made.

The baking procedure was the same as described in Example 4 using the recipe described in Table 5.

TABLE 5

| Recipe | |
|---|---|
| Ingredients | Amount |
| Sponge | |
| Flour (Wigwam, US white flour) | 70 g |
| Water | 40.6 g |
| Soybean oil | 3 g |
| Yeast dry matter (See 4) | 2.15 g |
| Dough | |
| Flour (Wigwam, US white flour) | 30 g |
| Water | 20.4 g |
| Sugar | 5 g |
| Salt | 2 g |
| Calcium Propionate | 0.35 g |
| Ascorbic acid | 60 ppm |

After baking, the bread was removed from the pans and allowed to cool down for 10 min at room temperature after which they were placed in a sealed plastic bag and stored at room temperature until analyzed for crumb firmness.

Crumb firmness was evaluated using a TA.XT plus Texture Analyzer (Stable Micro Systems, Surrey, UK) equipped with a spherical probe (25.4 mm diameter).

The bread sample was compressed 40% of the original height at a speed of 1.7 mm/s. Crumb firmness in grams at 25% compression was used to characterize the bread crumb firmness.

Results

TABLE 6

Effect of different yeast strains on change in Firmness (g) measured with texture analyzer

| | Name | Day 1 | Day 3 | Day 7 |
|---|---|---|---|---|
| 1 | Control (Standard yeast - Fleischmann) | 117 | 293 | 428 |
| 2 | Standard yeast + Novamyl 10000 BG | 113 | 221 | 367 |
| 3 | Yeast expressing SEQ ID NO: 2, three cassettes | 75 | 160 | 227 |
| 4 | Yeast expressing SEQ ID NO: 1, three cassettes | 102 | 283 | 403 |
| 5 | Yeast expressing SEQ ID NO: 3, three cassettes + markers | 153 | 185 | 190 |

It can be seen from Table 6 that yeast expressing anti-staling/freshness enzymes were all better than the control; and the yeast expressing SEQ ID NO:3 was much better than adding 50 ppm Novamyl 10000 BG at day 7.

The invention claimed is:

1. A process for producing a dough, comprising adding a recombinant Saccharomyces cerevisiae cell comprising between one to four copies of a heteroloqous polynucleotide each maintained as a chromosomal integrant, wherein each heteroloqous polynucleotide comprises at least one polynucleotide encoding a maltogenic amylase having at least 85% sequence identity to amino acids 20-705 of SEQ ID NO:1, to dough ingredients and making the dough.

2. A process for producing a dough, comprising adding the recombinant *Saccharomyces cerevisiae* cell of claim 1, wherein the maltogenic amylase has at least 95% sequence identity to amino acids 20-705 of SEQ ID NO:1, to dough ingredients and making the dough.

3. A process for producing a dough, comprising adding the recombinant *Saccharomyces cerevisiae* cell of claim 1, wherein the heteroloqous polynucleotide encodes a maltogenic amylase consisting of amino acids 20-705 of SEQ ID NO:1, to dough ingredients and making the dough.

4. A process for producing a dough, comprising adding the recombinant *Saccharomyces cerevisiae* cell of claim 1, which further comprises a second heterologous polynucleotide encoding a beta-amylase having at least 85% sequence identity to SEQ ID NO:4, to dough ingredients and making the dough.

5. A process for producing a dough, comprising adding the recombinant *Saccharomyces cerevisiae* cell of claim 1, which further comprises a second heterologous polynucleotide encoding a glucan 1,4-alpha-maltotetrahydrolase having at least 85% sequence identity to SEQ ID NO:5, to dough ingredients and making the dough.

6. The process of claim 1, wherein a baked or a steamed product is made from the dough.

7. The process of claim 6, wherein an enzyme selected from the group consisting of amylase, glucanase, galactanase, mannanase, aminopeptidase, alpha-amylase, carboxypeptidase, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, phospholipase, mannosidase, oxidase, pectinolytic enzymes, peptidoglutaminase, peroxidase, phytase, glucose oxidase, polyphenoloxidase, proteolytic enzyme, ribonuclease, transglutaminase and xylanase is added to the dough.

8. The process of claim 1, wherein one of the dough ingredients is flour.

9. The process of claim 8, wherein the flour is selected from the group consisting of wheat, emmer, spelt, einkorn, barley, rye, oat, corn, sorghum, rice, millet, amaranth, quinoa, and cassava and any combinations thereof.

* * * * *